(12) United States Patent
Giri

(10) Patent No.: US 7,300,766 B2
(45) Date of Patent: Nov. 27, 2007

(54) POLYMERIC AMMONIUM AND OR PHOSPHONIUM SALTS HAVING ADDED π-ELECTRONS AND HIGHER MOLECULAR WEIGHT AS ENHANCERS FOR CHEMILUMINESCENT SYSTEMS

(76) Inventor: Brij P. Giri, 1197 Rochester Rd., Suite 1, Troy, MI (US) 48083

( * ) Notice: Subject to any disclaimer, the term of this patent is extended or adjusted under 35 U.S.C. 154(b) by 355 days.

(21) Appl. No.: 10/515,641

(22) PCT Filed: May 23, 2003

(86) PCT No.: PCT/US03/16584

§ 371 (c)(1),
(2), (4) Date: Nov. 19, 2004

(87) PCT Pub. No.: WO03/099802

PCT Pub. Date: Dec. 4, 2003

(65) Prior Publication Data

US 2005/0233303 A1    Oct. 20, 2005

Related U.S. Application Data

(60) Provisional application No. 60/382,814, filed on May 23, 2002.

(51) Int. Cl.
   *C12Q 1/66* (2006.01)
(52) U.S. Cl. .......................... 435/8; 436/172; 549/220; 549/221; 549/332

(58) Field of Classification Search .................... 435/8, 435/19, 960; 252/700; 436/172; 549/220, 549/221, 332
See application file for complete search history.

(56) References Cited

U.S. PATENT DOCUMENTS

| | | | | |
|---|---|---|---|---|
| 5,547,836 A | * | 8/1996 | Bronstein et al. | 435/6 |
| 5,637,747 A | * | 6/1997 | Bronstein et al. | 558/194 |
| 5,650,099 A | * | 7/1997 | Akhavan-Tafti et al. | 252/700 |
| 5,777,135 A | * | 7/1998 | Akhavan-Tafti et al. | 549/332 |
| 6,602,679 B2 | * | 8/2003 | Giri | 435/28 |

FOREIGN PATENT DOCUMENTS

| | | | |
|---|---|---|---|
| GB | 2233451 A | * | 1/1991 |
| JP | 03053897 A2 | * | 3/1991 |

* cited by examiner

Primary Examiner—Ralph Gitomer
(74) Attorney, Agent, or Firm—The Weintraub Group, PLC

(57) ABSTRACT

A compound for enhancing the light output of a chemiluminescent system and, in particular, a stabilized, triggerable 1,2-dioxetane, is obtained by reacting a polyvinylbenzyl halide and a bilinker with either a trisubstituted amine or trisubstituted phosphine. A fluorescent molecule may be attached to polymer along with the trisubstituted amine or trisubstituted phosphine. Also, the benzyl halide may be reacted with a π-electron donor, such as a vinyl naphthalene or vinylanthracene to form a co-polymer which is polymerizable with the trisubstituted amine and/or trisubstituted phosphine. By controlling the reaction parameters it is possible to obtain either a water-soluble or partial water soluble or insoluble compound crosslink polymer.

17 Claims, No Drawings

POLYMERIC AMMONIUM AND OR PHOSPHONIUM SALTS HAVING ADDED π-ELECTRONS AND HIGHER MOLECULAR WEIGHT AS ENHANCERS FOR CHEMILUMINESCENT SYSTEMS

CROSS REFERENCE TO RELATED APPLICATIONS

This application is a National Stage application filed under Rule 371 based on PCT/US03/16584 filed May 23, 2003, which claims benefit to 60/382,814 filed May 23, 2002.

BACKGROUND OF THE INVENTION

1. Field of the Invention

The present invention relates to polymers used with light producing stabilized 1,2-dioxetanes or other chemiluminescent compounds to produce enhanced chemiluminescence. More particularly, the present invention relates to polymeric ammonium and phosphonium salts with or without fluorescent molecules and methods of manufacture therefor. Even more particularly, the present invention concerns polymeric phosphonium and ammonium salts prepared from the reaction of (a) polyvinylbenzyl chloride having (1) added π-electrons or (2) higher molecular weight and/or (3) both and (b) trisubstituted amines and/or trisubstituted phosphines. The present invention, also concerns describes the use of these new polymers to enhance the chemiluminescent light produced by the decomposition of stabilized 1,2-dioxetanes which can be destabilized by the action of an enzyme or a chemical.

2. Prior Art

As is known to those skilled in the art to which the present invention pertains, enhancers are substances which increase the amount of chemiluminescence emitted by a 1,2-dioxetane or other chemiluminescent system. The best known chemiluminescent reactions are those which employ, stabilized, enzyme-triggerable 1,2-dioxetanes, acridanes, acridinium esters, luminol, isoluminol and derivatives thereof or lucigenin. These chemiluminescent compounds are generally denoted in the art as either agents, reactants or substrates. Enhanced chemiluminescence means that the total light emitted, the maximum light intensity and/or the ratio of light intensity of the reaction compared to the background is greater than that observed in the absence of the enhancer.

The effect of a non-chemiluminescent donor on luminescence has been found to be profoundly influenced by changes in the ratio between the luminescent donor and the non-luminescent donor. For example, the increase of light emission caused by the addition of o-phenylenediamine to a peroxidase-based system is accompanied by an accelerated formation of the blue dimer, thus speeding up the rate-limiting step. Further, at constant pyrogallol concentrations, it has been found that the addition of o-phenylenediamine never causes an increase in the integrated luminescence yield, although the velocity of the luminescent process can be accelerated, thus giving a higher luminescence peak. On the other hand incorporation of p-phenylenediamine into a peroxidase-purpurogallin-hydrogen peroxide system results in an eight-fold enhancement of light emission [M. Halmann, B. Velan, T. Sery and H. Schupper, *Photochem. Photobiochem.*, 30, 165 (1979)]. The effect of other factors such as pH change, heavy water, radical scavengers and the addition of other enhancers on the enhancement of chemiluminescence of peroxidase-catalyzed reactions has been reported in the literature. See, inter alia, L. Ewetz and A. Thore, Anal. Biochem., 71, 564 (1976); J. K. Wong and M. L. Salin, *Photochem. Photobiol.*, 33, 737 (1981); H. P. Misra and P. M. Squatrioto, *Arch. Biochem. Biophys.*, 215, 59 (1982); G. H. G. Thorpe, L. J. Kricka, E. Gillespie, S. Moseley, R. Amess, N. Bagget and T. P. Whitehead, Anal. Biochem., 145, 96 (1985); T. J. N. Carter, C. J. Groucutt, R. A. W. Stott, G. H. G. Thorpe and T. P. Whitehead, European Patent, No. 87959 (1982); G. H. G. Thorpe, L. J. Kricka, S. B. Moseley and T. P. Whitehead, *Clin. Chem.* (Winston-Salem, N.C.), 31, 1335 (1985); L. J. Kricka, G. H. G. Thorpe and T. P. Whitehead, European Patent No. 116454 (1983) and U.S. Pat. No. 4,598,044.

Similarly, numerous assay enhancers have been employed in conjunction with and in a peroxidase-catalyzed reaction of luminol or acridane to increase the intensity and duration of light emission. These enhancers include benzothiazole derivatives such as 6-hydroxybenzothiazole derivatives, dehydroluciferin, firefly luciferin, substituted phenols such as p-iodophenols, p-phenylphenol or 2-naphthol, and aromatic amines such as p-phenylenediamine or tetramethyl benzidine. Other compounds which function as enhancers for chemiluminescent oxidation of amino-substituted cyclic acylhydrazide by a peroxidase include N,N-dimethylindoaniline, 2,6-dichlorophenoline-o-cresol, phenolindophenol, N-methyl-phenathiazine and a combination of phenolindolphenol and N-methylphenathiazine, as disclosed in U.S. Pat. No. 5,171,668 and in PCT/US97/06422 (1999), the disclosures of which are hereby incorporated by reference.

The chemiluminescence enhancing effect of 2-hydroxy-9-fluoro-4-hydroxy-3-[3-(4-hydroxyphenyl)-1-oxo-2-propenyl]-2H-1-benzopyrene-2-one and substituted oxazole derivatives in a peroxidase-oxidant-luminol or isoluminol system has, also, been reported. See, U.S. Pat. No. 5,206, 149. Similarly, surfactants including nonionic, cationic and anionic as well as polymeric compounds are known to affect the light producing efficiency of peroxidase-catalyzed reactions, as reported by L. J. Kricka and M. Deluca, *Arch. Biochem. Biophys.*, 217, 674 (1983); T. Goto and H. Fukatsu, Tet. Letts., 4299 (1969); and K. Sasamoto and Y. Ohkura, *Chem. Pharm. Bull.*, 39, 411 1991). The major advantage of enhanced assays is that the intensity of light emission may be greater than 1000-fold that of an un-enhanced reaction. Also, conditions can be employed under which light emission is prolonged and decay is slow.

The full mechanism for the oxidation of cyclic acylhydrazides and acridanes by the combination of peroxide and peroxidase enzyme and the light enhancement by enhancers is not known. However, many compounds reported to increase light emission from chemiluminescent and bioluminescent systems do not enhance the peroxidase-catalyzed system under reported conditions, but 6-hydroxybenzothiazole and phenol derivatives produce dramatic increases in light intensity, thereby suggesting they operate by a different mechanism. See, for example, T. P. Whitehead, G. H. G. Thorpe, T. J. N. Carter, C. Groucutt and L. J. Kricka, Nature (London), 305, 158 (1983); H. W. Yurow and S. Sass, *Anal. Chim. Acta.*, 88, 389 (1977); D. E. Bause and H. H. Patterson, *Anal. Chem.*, 51, 2288 (1985); F. Kohen, J. B. Kim, G. Barnard and H. R. Linder, *Steroids*, 36, 405 (1980); H. R. Schroeder, P. O. Vogelhut, R. J. Carrico, R. C. Boguslaski and R. T. Buckler, *Anal. Chem.*, 48, 1933 (1976), and M. L. Grayeski and E. Woolf, in "*Analytical Application of Bioluminescence and Chemiluminescence*" (L. J. Kricka, P. E. Stanley, G. H. G. Thorpe and T. P. Whitehead, eds), p. 565, Academic Press, Orlando, 1984.

Similarly, numerous enhancers have been employed in conjunction with the use of stabilized 1,2-dioxtanes. The enhancement of chemiluminescence from a stable 1,2-dioxetane triggered decomposition by an enzyme in the presence of water-soluble substances including a long chain aliphatic ammonium surfactant and a fluorescent compound has been taught in U.S. Pat. No. 4,959,182. According to this reference, micelles containing cetyltrimethyl-ammonium bromide (CTAB) and a fluorescent molecule attached to a long chain hydrocarbon, 5-(N-tetradecanoyl) aminofluorescein, capture the intermediate hydroxy-substituted 1,2-dioxetane, which is destabilized under basic pH of buffer to decompose, and leads to a 400-fold increase in chemiluminescence efficiency. Enhancement occurs by virtue of an efficient intermolecular energy transfer process from the anionic form of the excited state ester to the fluorescent compound, which is held in close proximity, and the hydrophobic environment created by the surfactant.

The synthesis of polymeric quaternary ammonium compounds and polymeric benzyltrialkylphosphonium salts is well known in the literature, see, inter alia, U.S. Pat. Nos. 2,780,604; 3,178,396; 3,770,439; 3,898,088; 4,308,335; 4,340,522; 4,424,326; 4,563,411; and 3,239,519. Recently, these polymers have been used as an enhancer to enhance the light output of stabilized 1,2-dioxetanes when triggered to destabilize either chemically or enzymatically. See U.S. patent application Ser. No. 09/883,586, the disclosure of which is hereby incorporated by reference.

The effect of substitution on the solubility of certain polyvinybenzyl chloride polymers has been described in U.S. Pat. No. 4,308,335. According to this reference, the quaternary nitrogen polymers of the reference are prepared by the reaction of polyvinylbenzyl chloride and a tertiary amine. The structure of the polymer can be shown as below:

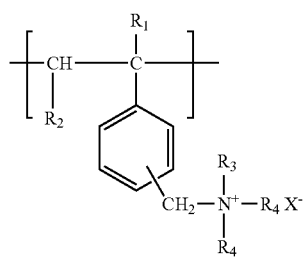

(1)

Where $R_1$, $R_2$, $R_3$, $R_4$ and $R_5$ are, individually, either hydrogen or alkyl having from 1 to 20 carbon atoms. When the quaternary nitrogen of formula (1) has a long alkyl chain i.e. more than a five carbon chain, the resulting cationic polymer is insoluble in water but is soluble in organic solvents.

In the same way when polyvinylbenzyl chloride is treated with trialkylphosphine, the following polymer is obtained:

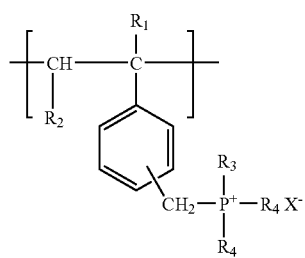

(2)

When the quaternary nitrogen of formula (2) has a long alkyl chain, i.e. more than five carbon atoms, the resulting cationic polymer is water-insoluble. Other water-insoluble or partially water-insoluble polymers can be synthesized by the combination of two or three different trialkylphosphines. These polymers have shown excellent enhancement of chemiluminescent of stabilized 1,2-dioxetanes compared to water-soluble polymers.

Water-soluble polymeric quaternary ammonium salts when used alone or when admixed with fluorescein, as disclosed in U.S. Pat. Nos. 4,978,614; 5,145,772; 5,547,836; 5,593,828 and 5,654,154 and polyvinylbenzyl-trialkylphosphonium salts used alone or admixed or covalently attached to fluorescent molecules as described in U.S. Pat. Nos. 5,393,479; 5,431,845; 5,474,725; 5,582,775, have been taught to enhance chemiluminescence efficiency of stable 1,2-dioxetanes. Structurally, these polymers can be shown as:

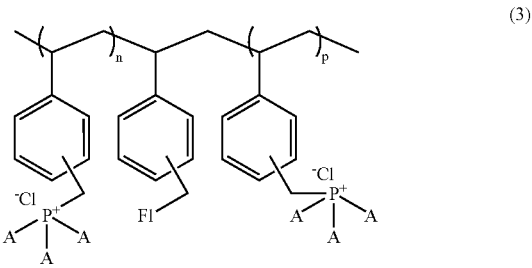

(3)

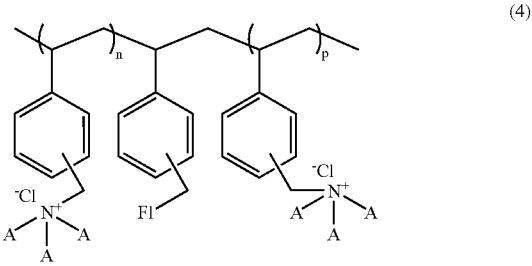

(4)

where A is selected from the group consisting of lower alkyl containing 1 to 20 carbon atoms, aryl, aralkyl or alkyaryl groups, n and p are each an integer of from about 3 to about 15 and Fl is a fluorescent molecule attached covalently to the phenyl ring or is admixed with the polymer molecules.

The attachment of Rose-Bengal, which has structural similarity to fluorescein, to polymeric materials, has, also, been reported in literature (J. Am. Chem. Soc., 97, 3741, 1975). This polymer is used to produce singlet oxygen when irradiated with visible light in the presence of oxygen in organic solvents and can be filtered after use. The dye covalently attached to the polymer can be excited with visible light and the excited dye transfers its energy to the molecular oxygen to produce singlet oxygen which is highly reactive to unsaturated organic molecules.

However, the prior art does not disclose the use of water-insoluble or partially water-soluble polymers or organic solvent soluble polymers of ammonium and phosphonium salts with or without fluorescent molecules as an enhancer for stabilized 1,2-dioxetanes and, other chemiluminescent substrates.

The prior art, also, does not teach cross-linked polymers, having added π-electrons or higher molecular weight or both, derived from polyvinylbenzy halide or copolymers of polyvinyl naphthalene and polyvinyl benzylhalide and bilinkers.

It is to this to which the present invention is directed as detailed below.

SUMMARY OF THE INVENTION

The present enhancers are particularly useful in conjunction with stabilized, triggerable 1,2-dioxetanes because they create a hydrophobic environment around 1,2-dioxetanes and act like an organic media in aqueous media. Because the quantum yield of 1,2-dioxetanes in aqueous media is very poor, by providing a hydrophobic region, light-quenching water reactions are reduced or avoided all together, resulting in an overall improvement of chemiluminescence.

The present polymers are synthesized by the reaction of polyvinylbenzyl halide and organic bilinkers having saturated or unsaturated carbons which are attached to various trisubstituted amines or trisubstituted phosphines.

Although not wishing to be bound by any theory it appears that the cross-linking is random, although other structures are possible. The structure of the assumed polymer presumably depends on the amount of bilinker used in the reaction mixture and the temperature of the reaction mixture.

The degree of cross-linking between polymers and bilinker is regulated by dissolving the polymer and different amounts of bilinker in a suitable organic solvent. It has been observed that when more than 20% by weight of bilinker is used, the cross-linked polymer is insoluble in organic solvents. The reason for insolubility is presumably due to the high molecular weight of the resulting polymer. For proper cross-linking, the ratio by molecular weight of polymer and bilinker may be one to one i.e. if the molecular weight of polymer is 50,000 and the molecular weight of the bilinker for N,N,N',N'-tetramethy-2-butene-1,4-diamine is 142, the ratio of polymer and bilinker can be 50,000:142. Cross-linking is performed in such a way as to keep the polymer soluble in either an organic solvent or in aqueous media.

In preparing the present enhancer, the cross-linked polymer is reacted with either a trisubstituted phosphine or trisubstituted amine or mixtures thereof. It should be noted that, optionally, a fluorescent molecule may be attached covalently; attached to a phenyl ring or admixed with the phosphine and/or amine. In carrying out the phosphine and/or amine addition generally the polymer and the phosphine and/or amine will be present in a one to one or higher molecular weight ratio to the polymer.

The $\pi$-electron is introduced into the polymer by copolymerization of vinylic aromatic hydrocarbon and vinylbenzylhalide. Useful vinyl aromatic hydrocarbons include, for example, substituted or unsubstituted vinyl naphthalene; substituted, vinyl anthracene, and the like and mixtures thereof.

For a more complete understanding of the present invention reference is made to the following detailed description and accompanying illustrative examples.

DESCRIPTION OF THE PREFERRED EMBODIMENTS

Generally, the present invention provide new cross-linked or $\pi$-electron added or higher molecular weight polymers which can be used to increase the light output of chemiluminescent 1,2-dioxetane and other chemiluminescent systems when they decompose chemically or enzymatically in aqueous media and methods of synthesis and use thereof.

The enhancers are particularly useful in conjunction with stabilized, triggerable 1,2-dioxetanes because they create a hydrophobic environment around 1,2-dioxetnes and act like a organic media in aqueous media. Because the quantum yield of 1,2-dioxatanes in aqueous media is very poor, by providing a hydrophobic region, light-quenching water reactions are reduced or avoided all together, resulting in an overall improvement of chemiluminescence.

Chemiluminescent 1,2-dioxetanes

In copending U.S. patent application Ser. Nos. 09/883,586, the disclosure of which is incorporated by reference, there is provided a detailed history of the evolution of chemiluminescent compounds and their uses which for the sake of brevity need not to be repeated herein.

However, for purposes of the ensuing description of the present invention, it should be noted that the enzyme cleavable 1,2-dioxetanes of formulae (1), (2), (3), (4) and (5) shown below and disclosed in the copending application have been commercialized and used in immunoassays, Southern blotting, Northern blotting, Western blotting, plaque/colony lifts and DNA sequencing.

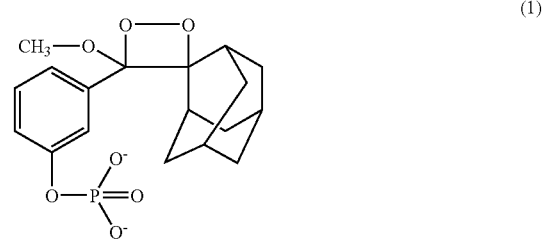

(1)

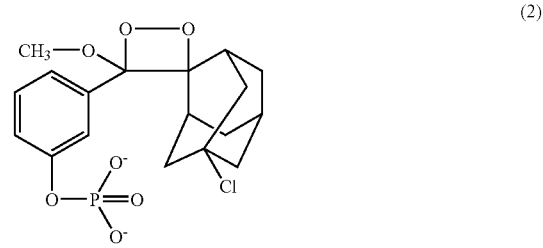

(2)

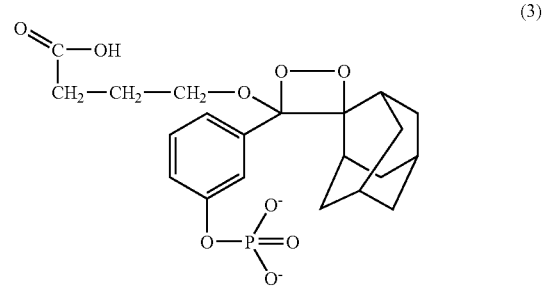

(3)

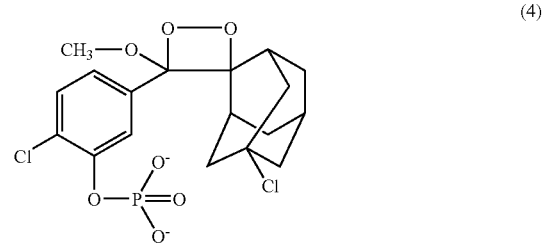

(4)

-continued

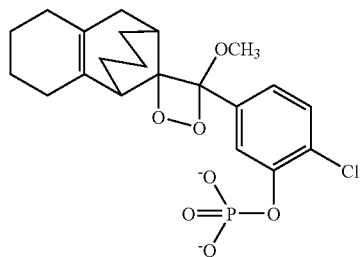
(5)

The 1,2-dioxetanes of formulae (2) and (4) with chlorosubstitution in the adamantane ring or in both the adamantane ring and the phenyl ring demonstrate better results in DNA sequencing when compared to the dioxetane of formula (1). Dioxetane (3) is more soluble in an aqueous system than those of formulae (1), (2) and (4) when a $CH_3$ group is replaced with a $CH_2CH_2CH_2COOH$ and dioxetane (5) with chlorosubstitution in the benzene ring and unsaturation in the adamantane ring and, specifically tricyclo [7.3.1.0 $^{2,7}$]tridec-2,7-ene-1 3-one has demonstrated greater superiority in sensitivity on membranes as well as in other applications.

The present polymers are synthesized by the reaction of polyvinylbenzyl halide and organic bilinkers having saturated or unsaturated carbons which are attached to various trisubstituted amines or trisubstituted phosphines.

The bilinkers used herein are selected from the group consisting of:

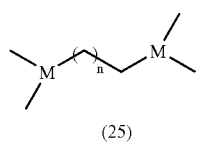
(a)
(25)

N or P or other element,

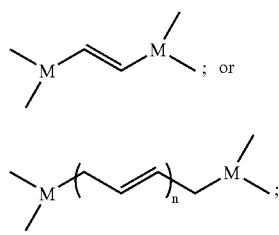
(26)
(27)

wherein n may be any integer from 1 to about 20 and M is either N or P or other element.

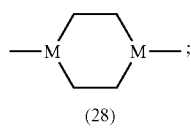
(b)
(28)

-continued

(29)

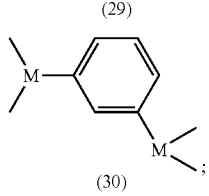
(30)

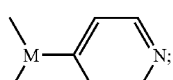
(31)

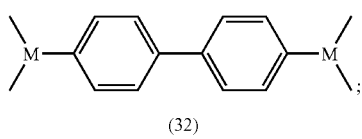
(32)

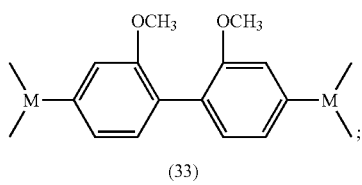
(33)

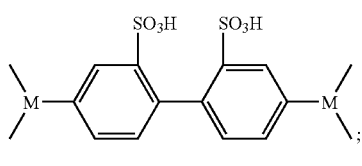
(34)

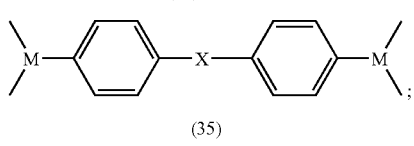
(35)

X is either N, S or P and M is as described above;

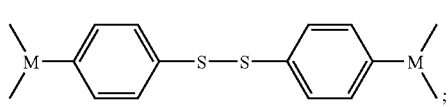
(c)
(36)

M is either N or P or other element

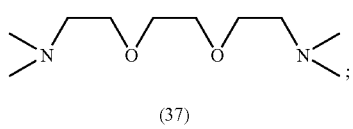
(d)
(37)

-continued

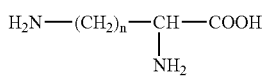
(e)

wherein n is an integer of from 1 to 20 carbon atoms;

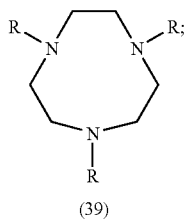
(f)

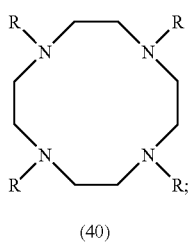
(40)

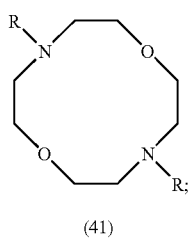
(41)

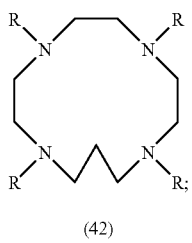
(42)

where R is an organic group and may be alkyl or substituted alkyl, alkylacid, arylalkyl, alklylaryl.

Preferably, the bilinker is selected from the group consisting of N,N,N'N'-tetramethyl-2-butene-1,4-diamine; N,N,N'N'-tetramethylbutane-1,4-diamine; 1,4-dimethyl piperazine; 1,4-phenylenediamine and mixtures thereof. The reaction product of polyvinylbenzyl chloride is cross-linked with N,N,N',N'-tetramethy-2-butene-1,4-diamine, can be shown as:

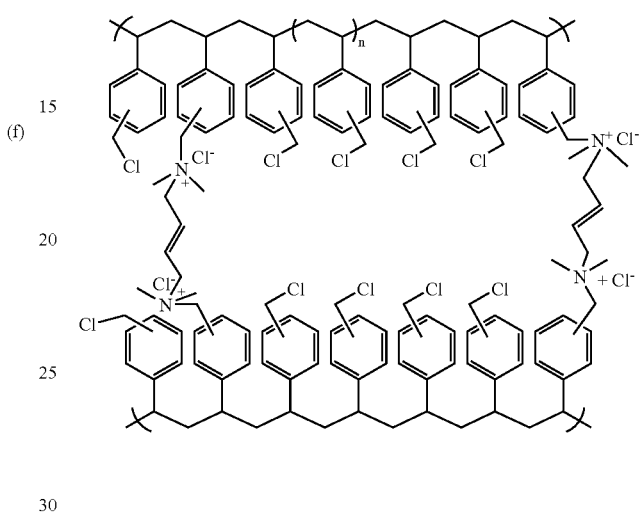
(43)

Although not wishing to be bound by any theory it appears that the cross-linking is random, other structures are possible. The structure of the assumed polymer presumably depends on the amount of bilinker used in the reaction mixture and the temperature of the reaction mixture.

The degree of cross-linking between polymers and bilinker is regulated by dissolving the polymer and different amounts of bilinker in suitable organic solvent. It has been observed that when more than 20% by weight of bilinkers is used, the cross-linked polymer is insoluble in organic solvents. The reason for insolubility is presumably due to the high molecular weight of the resulting polymer. For proper cross-linking, the ratio, by molecular weight of polymer and cross-linker may be one to one, i.e. if the molecular weight of polymer is 50,000 and the molecular weight of the bilinker for N,N,N',N'-tetramethy-2-butene-1,4-diamine is 142, the ratio of polymer and bilinker can be 50,000:142. Cross-linking is performed in such a way as to keep the polymer soluble in either an organic solvent or in aqueous media.

In preparing the present enhancer, the cross-linked polymer is reacted with either a trisubstituted phosphine or a trisubstituted amine or mixtures thereof. It should be noted that optionally, a fluorescent molecule may be attached covalently to the phenyl ring or admixed with the phosphine and/or amine. In carrying out the phosphine and/or amine addition, generally, the polymer and the phosphine and/or amine will be present in a one to one or higher molecular weight ratio to the polymer.

The trisubstituted amine enhancer can be shown as
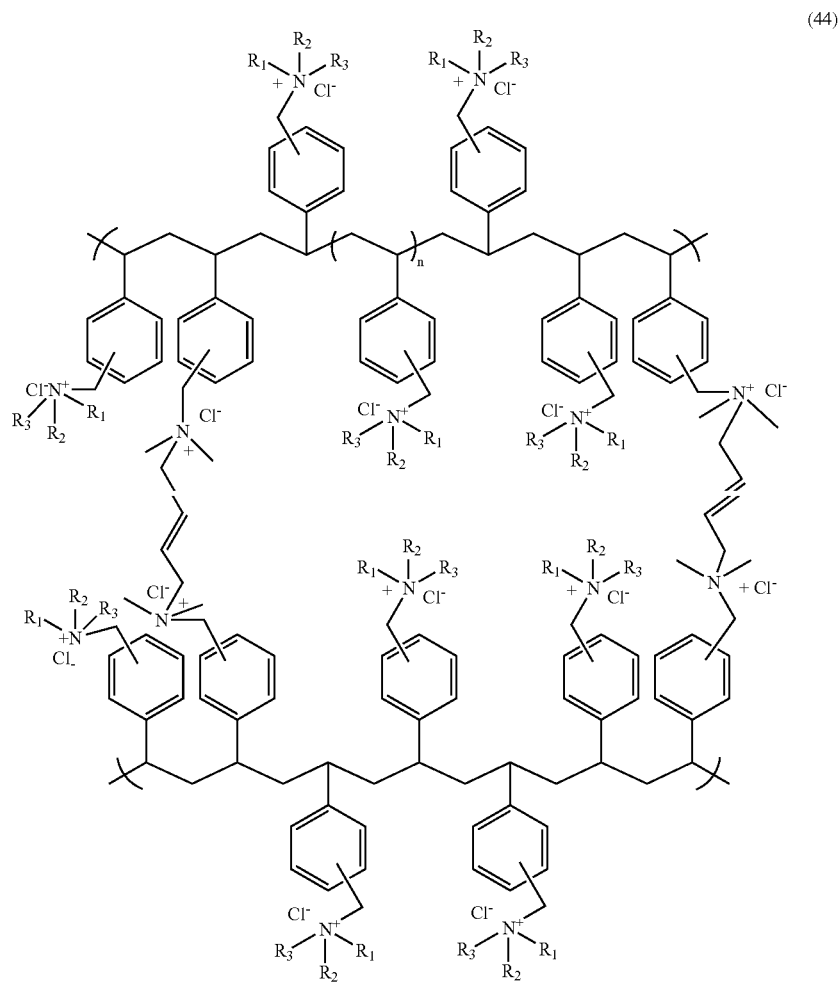
(44)
Similarly, the trisubstituted phosphine enhancer can be shown as;
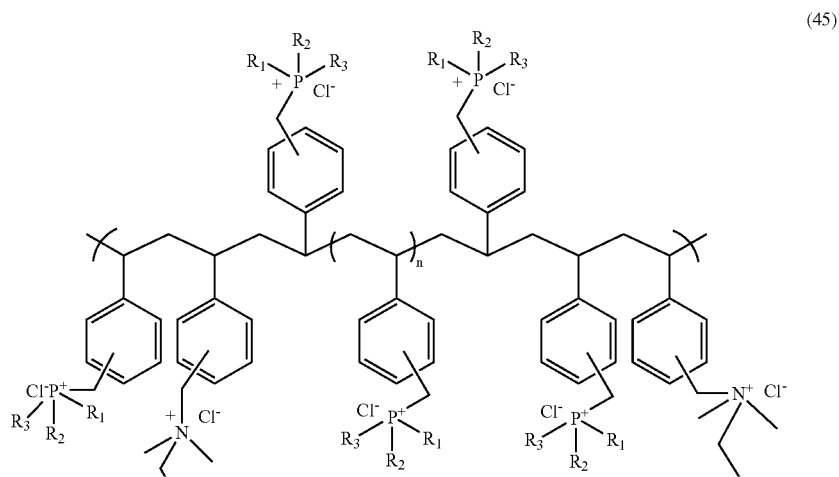
(45)

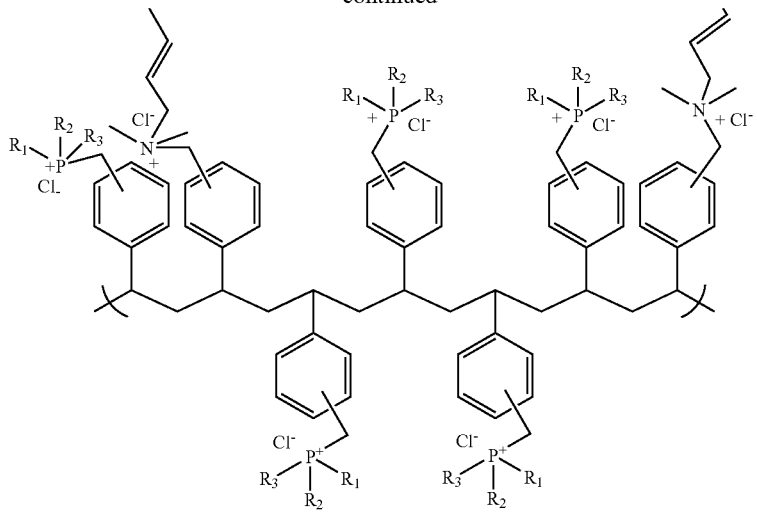

with respect to formulae (44) and (45), $R_1$, $R_2$ and $R_3$, individually, as described above.

When the cross-linked polymers are attached to the fluorescent molecules, enhancement occurs by virtue of an efficient intermolecular energy transfer process from the anionic form of the excited state ester to the fluorescent molecule which is attached covalently to the polymer. The emitted light from the fluorescent molecule has a different wavelength compared to direct emission from the excited state of the ester produced by the decomposition of the destabilized 1,2-dioxetane or other chemiluminescent compounds. The light output may be much higher if the energy transfer from the excited ester to the fluorescent molecule is very efficient and the fluorescence efficiency of the fluorescent molecules is higher compared to excited ester. The most probable structure of cross-linked polymer can be shown as:

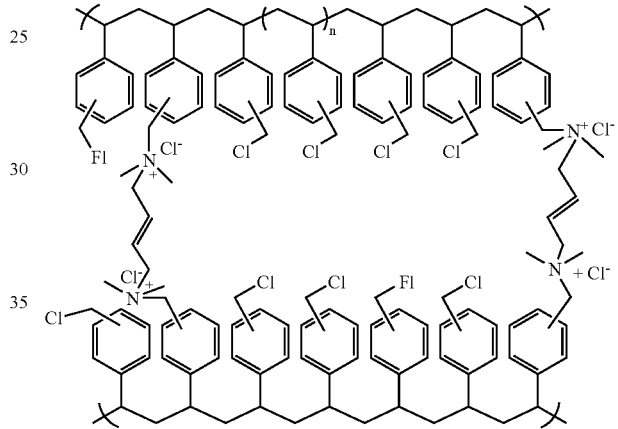

(46)

where n is as discussed above.

As noted above, fluorescent molecules containing cross-linked polymers can be attached to different molecules of trisubstituted amines such as tributyl amine, trihexyl amine and a trisubstituted phosphine such as triethyl phosphine, trioctylphosphine or mixtures thereof. Generally, these cross-linked enhancers can be represented as:

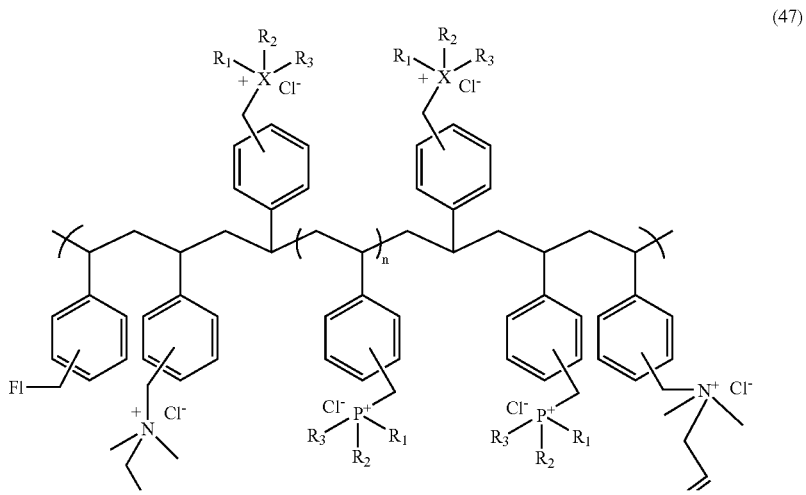

(47)

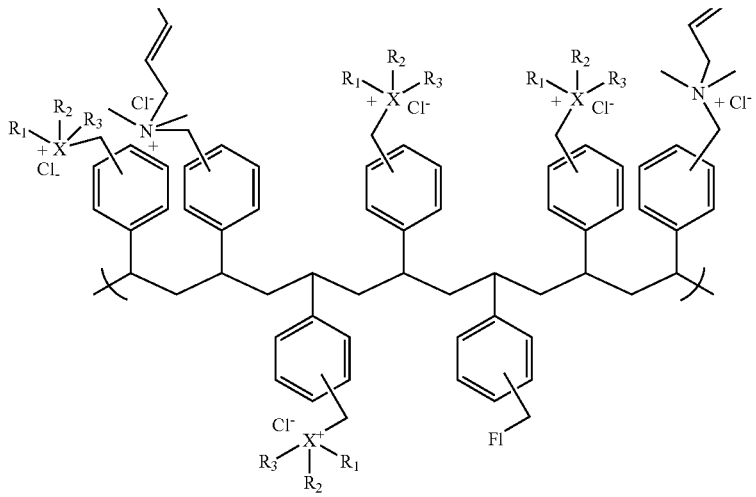

wherein X is N, P or other elements such as arsenic or antimony; each of $R_1$, $R_2$, and $R_3$ is either a straight or branched chain substituted or unsubstituted alkyl group having from 1 to 20 carbon atoms, inclusive, e.g., methyl, ethyl, n-butyl, t-butyl, hexyl, or the like: a straight or branched chain alkyl group having from 1 to 20 carbon atoms, inclusive; substituted or unsubstituted, with one or more hydroxy, alkoxy, e.g., methoxy, ethoxy, benzyloxy, aryloxy, e.g., phenoxy, amino or substituted amino, e.g., methylamino, amido e.g. acetamido or ureido, e.g. phenyl ureido; or fluoroalkane or p-fluoroaryl, e.g. heptafluorobutyl; substituted or unsubstituted monocycloalkyl group having 3 to 12 carbon ring atoms, inclusive, e.g., cyclohexyl or cuclooctyl, a substituted monocycloalkyl group having from 3 to about 12 carbon atoms, substituted with one or more alkyl, alkoxy, or fused benzo groups, e.g. methoxycyclohexyl or 1,2,3,4-tetrahydronaphthyl, a polycycloalkyl group having 2 or more fused rings, each having from 5 to 12 carbon atoms, inclusive, unsubstituted or substituted with one or more alkyl, alkoxy or aryl groups, e.g., 1-adamantyl or 3-phenyl-1-adamantyl, an aryl, alkaryl or aralkyl group having at least one ring and from 6 to 20 carbon atoms, unsubstituted or substituted with one or more alkyl, aryl, fluorine or hydroxy groups, e.g., phenyl, naphthyl pentafluorophenyl, ethylphenyl, benzyl, hydroxybenzyl, phenylbenzyl; at least two of $R_1$, $R_2$, and $R_3$, together with the quaternary nitrogen atom to which they may be bonded, can form a saturated or unsaturated, unsubstituted or substituted nitrogen-containing, nitrogen and oxygen-containing or nitrogen and sulfur-containing ring having from 3 to 5 carbon atoms, inclusive, and 1 to 3 heteroatoms, inclusive and which may be benzoannulated, e.g., 1-pyridinium, 1-(3-alkyl or aralkyl)imidazolium, morpholino, alkyl morpholinium, alkylpiperidinium, N-acetylpiperidinium, piperidino or acylpiperidino, benzoxazolium, benzthiazolium or benzamidazolium.

The π-electron is introduced into the polymer by copolymerization of a vinylic aromatic hydrocarbon and vinylbenzylhalide. Useful vinyl aromatic hydrocarbons include, for example, substituted or unsubstituted vinyl naphthalene; substituted vinyl anthracene and the like and mixtures thereof. Where the vinyl hydrocarbon is vinyl naphthalene and the halide is chloride, the co-polymer is assumed to below:

(48)

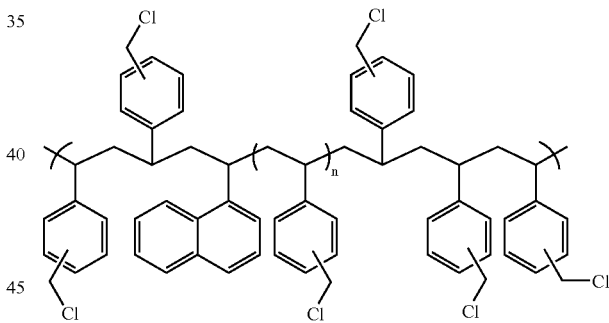

However the structure may vary depending on the amount of vinyl hydrocarbon used.

Generally, the reaction takes place from about room temperature 20° to about 100° C., in about 1 to about 200 hours or more. Generally, the hydrocarbon is present in an amount ranging from about 0.01% to about 50%, by weight, based on the total weight of the reaction mixture and, preferably from about 5% to about 10%. Usually, the reaction is carried out in the presence of a solvent, such as dimethylformamide, dimethyl sulfoxide, methylchloride, benzene, or the like and mixtures thereof.

The reaction of a α-electron containing co-polymer with trisubstituted amines or phosphines gives the following assumed polymer structure:

(49)

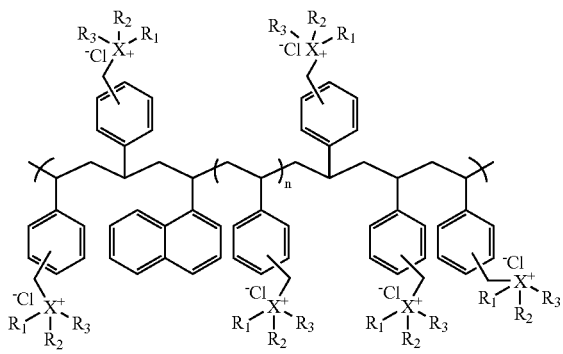

wherein X, $R_1$, $R_2$, and $R_3$ are as defined above.

When the co-polymer is attached to the fluorescent (Fl) molecule, the structure can be shown as:

(50)

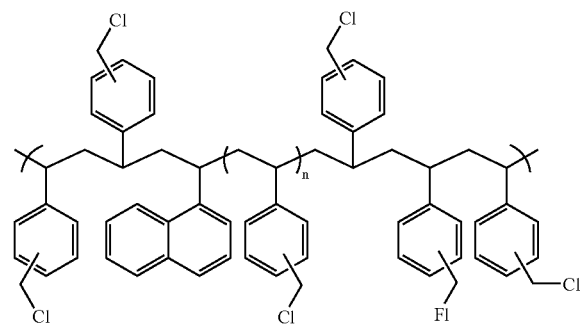

A fluorescent molecule attached copolymer, when treated with trisubstituted amines or trisubstituted phosphines, gives a polymeric material which structurally can be shown as:

(51)

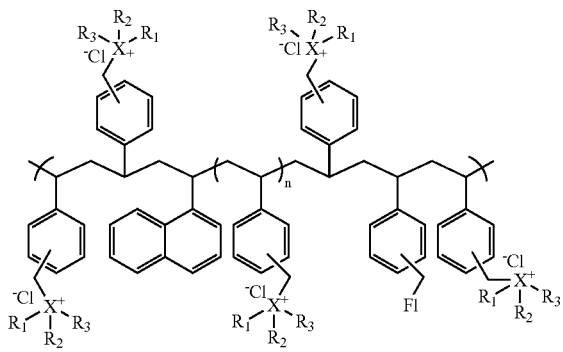

wherein X, $R_1$, $R_2$, and $R_3$ are as defined above.

The co-polymer may be further cross linked by reacting the resulting co-polymer with the bilinker to increase the π-electron density further. The resulting cross-linked co-polymer has the following structure:

(52)

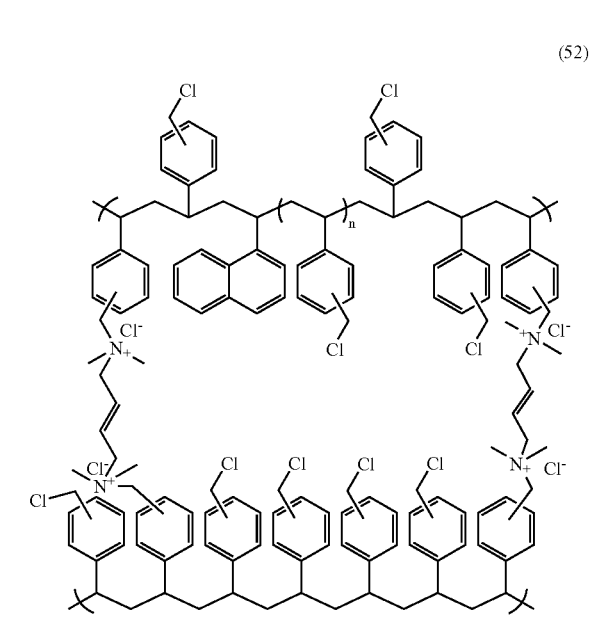

This further π-electron densification is carried out at a temperature of about room temperature to 100° C., preferably from about room temperature, i.e. about 20° C. to about 50° C., in about 1 to about 200 hours or more. Generally, the percentage of bilinker is present in an average amount ranging from about 0.001% to 20% based on the total weight and the percentage of copolymer is present in the amount ranging about 99.99 to about 80%, based on the total weight of the reaction mixture and, preferably in a 1:1 molecular weight ratio of co-polymer and bilinker. When the cross-linked co-polymer is reacted with trisubstituted amines or trisubstituted phosphines, the following polymers are obtained:

(53)
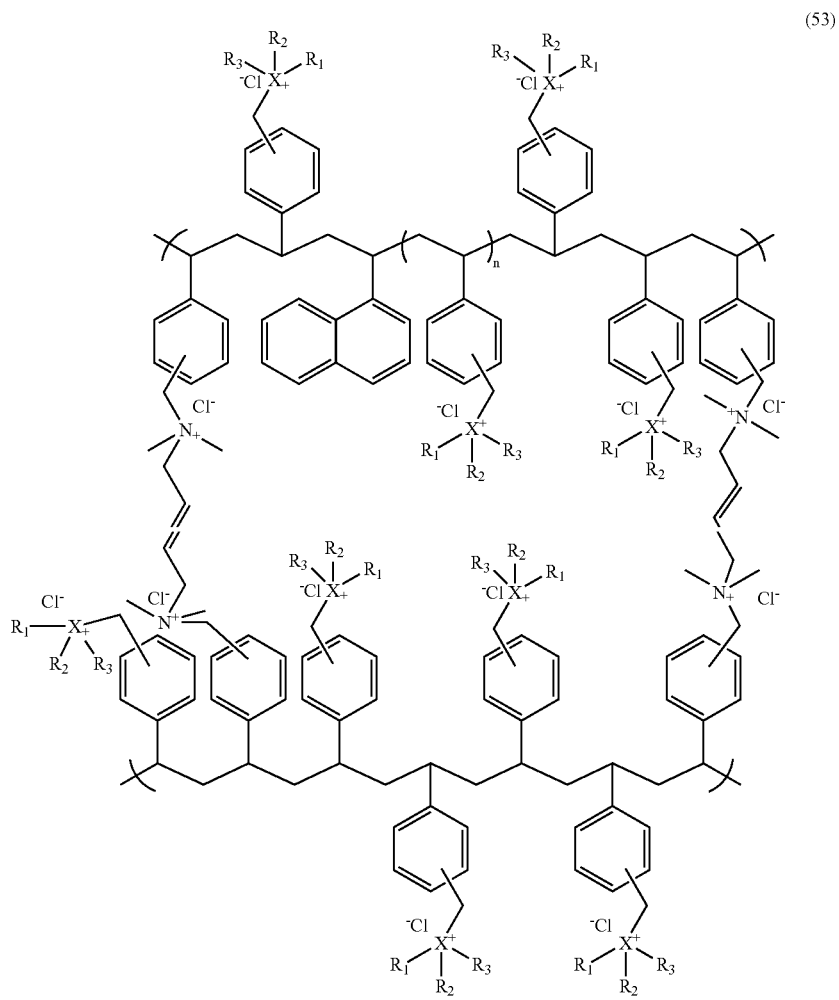
wherein X, $R_1$, $R_2$, and $R_3$ are as defined above.
When treated with a fluorescent molecule the vinylnaphthalene-vinyl benzyl halide co-polymer has the following structure:
(54)
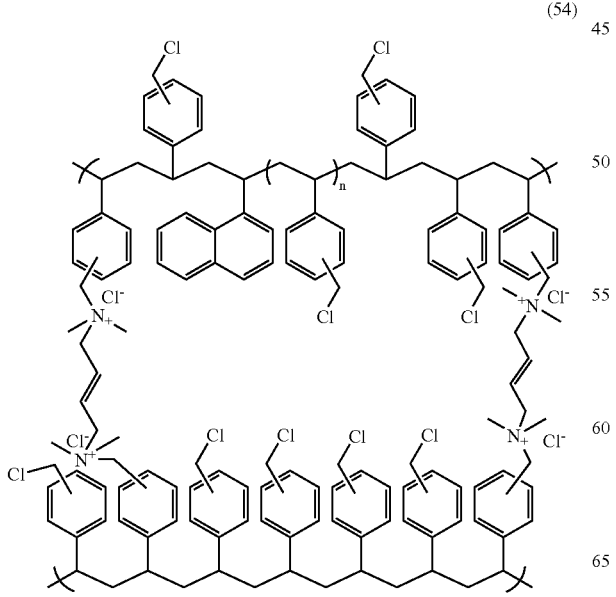

When the fluorescent molecule is reacted with a trisubstituted amine or trisubstituted phosphine, the resulting polymer can be shown as:

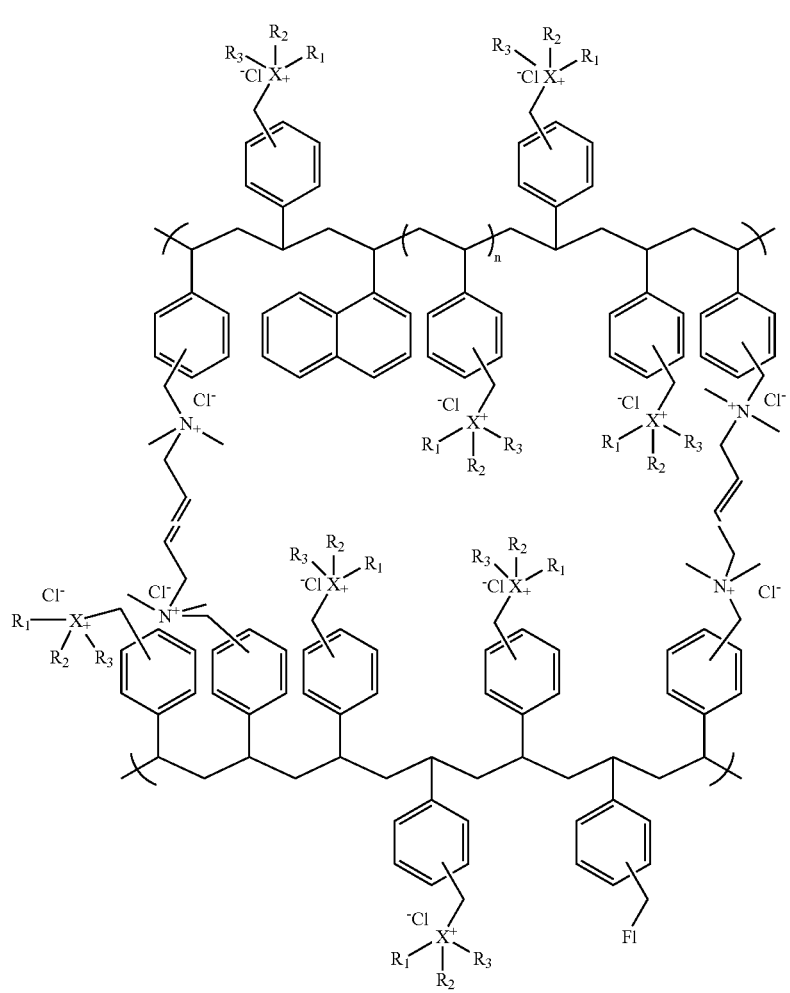

(53)

wherein X, $R_1$, $R_2$, and $R_3$ are as defined above.

In preparing the salt, the mixture of polyvinylbenzyl chloride or cross-linked polyvinylbenzyl chloride or co-polymer of polyvinylbenzyl chloride-polyvinyl naphthalene or cross-linked co-polymer of polyvinylbenzyl chloride-polyvinyl naphthalene with trisubstituted amines and phosphines is heated in a solvent such as DMSO or DMF.

For a more complete understanding of the present invention reference is made to the following, non-limiting, illustrative examples. In the examples all parts are by weight absent contrary indication.

Example I

This example illustrates the preparation of the reaction product of polyvinylbenzyl chloride and trioctylphosphine (Water insoluble or soluble in organic solvents polymer):

In a 500 ml round bottom flask was dissolved 5.0 parts of polyvinylbenzyl chloride in 150 ml of anhydrous dimethylformamide. To this was added 15 parts of trioctylphosphine in one portion under nitrogen. The reaction mixture was stirred at room temperature for 48 hours and then at 45° C. for 2-3 hours. The dimethylformamide was evaporated under reduced pressure at 50-55° C. and the viscous solid was washed with ether (3×200 mL) to give a solid, water-insoluble, organic solvent soluble product, which was dried under nitrogen to a yield of 11.0 parts.

Example II

Reaction of polyvinylbenzyl chloride and tributylphosphine and trioctylphosphine; partially water soluble polymer:

Following the procedure of Example I, 5.0 parts of polyvinylbenzyl chloride in 150 ml of anhydrous dimethylformamide was reacted with 15 parts of trioctylphosphine. After the reaction was completed, 5.0 parts of tributylphosphine was added in one portion. The reaction mixture was stirred at room temperature for 48 hours and at 45° C. for 2-3 hours. After cooling, the reaction mixture was poured into a 900 mL mixture of ether and hexane (1:1). The solvent was removed and the viscous solid was washed with ether (3×150 mL) to give a solid which was dried under nitrogen, to a yield of 9.7 parts of a partially water-soluble polymer.

Example III

Reaction of polyvinylbenzyl chloride and fluorescein, tributylphosphine and trioctylphosphine (partially water soluble fluorescent polymer):

In a 500 mL round bottom flask was dissolved 5.0 parts of polyvinylbenzyl chloride in 150 mL of anhydrous dimethylformamide to which was added 0.6 parts of fluorescein. The reaction mixture was heated at 70-75° C. for 48 hours. After cooling the mixture to room temperature, 15 parts of trioctylphosphine was added to the reaction flask in one portion under nitrogen and the reaction mixture was stirred at room temperature for 48 hours and then at 45° C. for 2-3 hours. Then 5.0 parts of tributylphosphine was added as described in Example I in one portion. After cooling, the mixture was poured into a 900 mL mixture of ether and hexane (1:1). The solvent was then removed and the residual viscous solid was washed with ether (3×150 mL) to give a solid which was dried under nitrogen to a of 9.25 parts.

Example IV

Cross-linked polymer of N,N,N',N'-tetramethyl-2-butene-1,4-diamine polyvinylbenzyl chloride (A):

In a 500 mL round bottom flask to a solution of 5.0 parts polyvinylchloride in 125 ml of anhydrous dimethyformamide was added 0.025 g of N,N,N',N'-tetramethyl-2-butene-1,4-diamine. The reaction mixture was stirred at room temperature for 24 hrs. and, then, for two additional hours at 50° C. in a water bath. The solvent was evaporated to dryness under reduced pressure. The resulting solid, polymer, was washed with 2×50 mL of ether and dried under nitrogen.

Using the procedure to obtain polymer A, a series of enhancers were prepared by reacting polymer A with tri-substituted amines, tri-substituted phosphines and fluorescent molecules. In each instance, polymer A is obtained in the manner described above. The following table, Table 1, sets forth the phosphine, amine and/or fluorescent molecule used to prepare the enhancer.

TABLE 1

| EXAMPLE | REACTANT | AMOUNT | POLYMER YIELD |
|---|---|---|---|
| 1 | 1 M Trimethylphosphine in toluene | 50 parts | 7.8 parts |
| 2 | Tributylphosphine | 10 parts | 9.5 parts |
| 3 | Trioctylphosphine | 15 parts | 11.5 parts |
| 4 | Fluorescein<br>Tributylphosphine | 0.6 parts<br>10 parts | 8.0 parts |
| 5 | Trioctylphosphine<br>Tributylphosphine | 2 parts<br>10 parts | 9.5 parts |
| 6 | Fluorescein<br>Trioctylphosphine<br>Tributylphosphine | 0.6 parts<br>2 parts<br>10 parts | 9.0 parts |

Example V

This example illustrates the preparation of a series of enhancers from a cross-linked polymer of N,N,N',N'-tetramethyl-2-butene-1,4-diamine and polyvinylbenzyl chloride:

Into 500 mL round bottom flask was added a solution of 5.0 parts polyvinylbenzyl chloride in 125 parts of anhydrous dimethyformamide, to which was added to the solution, 0.125 parts of N,N,N',N'-tetramethyl-2-butene-1,4-diamine. The reaction mixture was stirred at room temperature for 24 hrs. and for an additional two hours at 50° C. in a water bath. The solvent was, then, evaporated to dryness under reduced pressure. The resulting solid was washed with 2×50 parts of ether and dried under nitrogen.

Five parts of the so-obtained cross-linked polymer was dissolved in 150 parts of anhydrous dimethylformamide. Then 2.0 parts of trioctylphosphine was added to the reaction flask in one portion under nitrogen. The reaction mixture was stirred at room temperature for 48 hours and then at 45° C. for 2-3 hours. Thereafter, 15.0 parts of tributylphosphine was added thereto in one portion. The reaction mixture was stirred at room temperature for 48 hours and at 45° C. for 2-3 hours. After cooling, the reaction mixture was poured into a 900 mL mixture of ether and hexane (1:1). The solvent was removed and the viscous solid was washed with ether (3×150 ml) to give a solid which was dried under nitrogen to a yield of 9.3 parts.

To test the efficacy of attaching fluorescent molecules to the cross-linked polymer, five parts of the so-obtained cross-linked polymer was dissolved in 150 parts of anhydrous dimethylformamide. Then 0.6 parts of fluorescein was added in one portion and the reaction mixture was heated at 70°-75° C. for 48 hours. After cooling, the reaction mixture to room temperature 2.0 parts of trioctylphosphine was added to the reaction flask in one portion under a nitrogen blanket. The reaction mixture was stirred at room temperature for 48 hours and then an additional two to three hours at 45° C. Next 15 parts of tributylphosphine was added in one portion. The reaction mixture was stirred at room temperature for 48 hours and at 45° C. for an additional two to three hours. After cooling, the reaction mixture was poured into a 900 mL of a mixture of ether and hexane (1:1). The solvent was removed and the viscous solid was washed with ether (3×150 ml) to give a solid which was dried under nitrogen. The yield was 9.25 parts.

Example VI

A further series of cross-linked polymers were prepared by reacting polyvinylbenzyyl chloride with of N,N,N',N'-tetramethyl-2-butene-1,4-diamine. Thereafter, the resulting cross-linked polymer was reacted with either a trisubstituted phosphine, trisubstituted amine and/or fluorescent molecule. The cross linked polymer was prepared by adding into a 500 ml round bottom flask, 5.0 parts polyvinylbenzyl chloride in 125 parts of anhydrous dimethyformamide and a solution of 0.250 parts of N,N,N',N'-tetramethyl-2-butene-1,4-diamine. The reaction mixture was stirred at room temperature for 24 hours. and then 2 hours at 50° C. in a water bath. The solvent was evaporated to dryness under at 45° C. reduced pressure. The resulting solid was washed with 50 parts of ether and dried under nitrogen.

Five parts of the so-obtained cross-linked polymer was dissolved in 150 parts of anhydrous dimethylformamide. Next, 2.0 parts of trioctylphosphine was added to the reaction flask in one portion under a nitrogen blanket. The reaction mixture was stirred at room temperature for 48 hours and then at 45° C. for 2-3 hours. Thereafter, 15.0 parts of tributylphosphine was added in one portion. The reaction mixture was stirred at room temperature for 48 hours and at 45° C. for 2-3 hours. After cooling, the reaction mixture poured into a 900 mL mixture of ether and hexane (1:1). The solvent was removed and the viscous solid was washed with ether (3×150 ml) to give a solid which was dried under nitrogen. The yield was 9.0 parts.

Using the same procedure described above 5.0 parts of cross-linked polymer was dissolved in 150 parts of anhydrous dimethylformamide to which was added 0.6 parts of fluorescein in one portion. The reaction mixture was heated at 70°-75° C. for 48 hours. After cooling the reaction mixture to room temperature, 2.0 parts of trioctylphosphine was added to the reaction flask in one portion under a nitrogen blanket. The reaction mixture was stirred at room temperature for 48 hours and then at 45° C. for 2-3 hours. Then, 15 parts of tributylphosphine was added in one portion. The reaction mixture was stirred at room temperature for 48 hours and at 45° C. for 2-3 hours. After cooling, the reaction mixture was poured into a 900 parts of ether and hexane mixture (1:1). The solvent was removed and the viscous solid was washed with ether (3×150 parts) to give a solid which was dried under nitrogen. The yield was 8.75 parts.

Example VII

A series of cross-linked polymers was prepared from the following:

TABLE II

| Cross-linked polymer | Reactants Polyvinylbenzy halide | Reactants Bilinkers |
|---|---|---|
| A | Polyvinylbenzy halide 5.0 parts | N,N,N',N'-tetramethyl-2-butene-1,4-diamine 0.5 parts |
| B | Polyvinylbenzy halide 5.0 parts | N,N,N',N'-tetramethyl-2-butene-1,4-diamine 0.05 parts |
| C | Polyvinylbenzy halide 5.0 parts | 1,4-dimethylpiperazine 0.05 parts |
| D | Polyvinylbenzy halide 5.0 parts | 1,4-phenylenediamine 0.05 parts |
| E | Co-polymer poly(vinylbenzyl chloride-2-vinylnaphthalene) 95:5 poly | N,N,N',N'-tetramethyl-1,4-butanediamine 0.05 parts |
| F | Co-polymer poly(vinylbenzyl chloride-2-vinylnaphthalene) 95:5 poly | N,N,N',N'-tetramethyl-2-butene-1,4-diamine 0.05 parts |

Each of the cross-linked polymers, A through F, was, then, reacted with either a tri-substituted amine or phosphine with or without a fluorescent molecule.

The following tables, Tables III and IV, set forth the cross-linked polymer and the reactant(s). In each instance, depending on the reactant, the reaction conditions for attaching the amine or phosphine or incorporating the fluorescent molecule were as described above.

TABLE III

| Cross-linked polymer (amount in parts) | Tributyl phosphine) (amount in parts) | Trioctyl phosphine (amount in parts) | Fluorescein (amount in parts) | Yield (amount in parts) |
|---|---|---|---|---|
| A, (5) | 15 | 2 | | 9.5 |
| A, (5) | 15 | 2 | 0.6 | 8.5 |
| B, (5) | 10 | | | 9.0 |
| B, (5) | | 15 | | 10.25 |
| B, (5) | 10 | | 0.6 | 8.5 |
| B, (5) | 15 | 2 | | 10.5 |
| B, (5) | 15 | 2 | 0.6 | 9.5 |
| C, (5) | 10 | | | 8.0 |
| C, (5) | | 15 | | 10.0 |
| C, (5) | 10 | | 0.6 | 8.75 |
| C, (5) | 15 | 2 | | 10.0 |
| C, (5) | 15 | 2 | 0.6 | 9.0 |
| D, (5) | 10 | | | 7.75 |

TABLE III-continued

| Cross-linked polymer (amount in parts) | Tributyl phosphine) (amount in parts) | Trioctyl phosphine (amount in parts) | Fluorescein (amount in parts) | Yield (amount in parts) |
|---|---|---|---|---|
| D, (5) | | 15 | | 9.5 |
| D, (5) | 10 | | 0.6 | 9.0 |
| D, (5) | 15 | 2 | | 11.0 |
| D, (5) | 15 | 2 | 0.6 | 9.5 |
| E, (5) | 10 | | | 7.5 |
| E, (5) | | 15 | | 9.0 |
| E, (5) | 10 | | 0.6 | 9.25 |
| E, (5) | 15 | 2 | | 10.5 |
| E, (5) | 15 | 2 | 0.6 | 10.5 |
| F, (5) | 10 | | | 7.2 |
| F, (5) | | 15 | | 9.25 |
| F, (5) | 10 | | 0.6 | 9.0 |
| F, (5) | 15 | 2 | | 10.0 |
| F, (5) | 15 | 2 | 0.6 | 10.2 |

TABLE IV

| Cross-linked polymer (amount in parts) | Tributylamine (amount in parts) | Fluorescein (amount in parts) | Yield (amount in parts) |
|---|---|---|---|
| B, (5) | 10 | | 7.5 |
| B, (5) | 10 | 0.6 | 8.5 |
| C, (5) | 10 | | 7.0 |
| C, (5) | 10 | 0.6 | 8.75 |
| D, (5) | 10 | | 7.5 |
| D, (5) | 10 | 0.6 | 8.25 |
| E, (5) | 10 | | 7.75 |
| E, (5) | 10 | 0.6 | 8.75 |
| F, (5) | 10 | | 7.8 |
| F, (5) | 10 | 0.6 | 8.9 |

Example VIII

The added π-electron densities enhancers were prepared by the reaction of (polyvinylbenzylchloride-2-vinylnaphthalene) 95:5 poly and tributylamine with tributylphosphine or trioctylphosphine with or without fluorescein and/or mixtures thereof. Tables V, and VI below, set forth the reactants and the amounts thereof.

TABLE V

| Co-polymer (amount in parts) | Tributyl phosphine) (amount in parts) | Trioctyl phosphine (amount in parts) | Fluorescein (amount in parts) | Yield (amount in parts) |
|---|---|---|---|---|
| 5 | 10 | | | 7.35 |
| 5 | | 15 | | 9.45 |
| 5 | 10 | | 0.6 | 9.3 |
| 5 | 15 | 2 | | 10.15 |
| 5 | 15 | 2 | 0.6 | 9.8 |

TABLE VI

| Co-polymer (amount in parts) | Tributyamine (amount in parts) | Fluorescein (amount in parts) | Yield (amount in parts) |
|---|---|---|---|
| 5 | 10 | | 7.9 |
| 5 | 10 | 0.6 | 8.8 |

What is claimed is:

1. A composition for increasing the light output of a chemiluminescent composition comprising:
   the reaction product of a polyvinyl benzyl halide with either (a) a bilinker or (b) a π-electron donor to form a copolymer which copolymer is further reacted with a trisubstituted phosphine amine, a trisubstituted phosphine and mixtures thereof.

2. The composition of claim 1 wherein the bilinker is a saturated organic compound.

3. The composition of claim 1 wherein the bilinker is an unsaturated organic compound.

4. The composition of claim 1 wherein the bilinker is selected from the group consisting of:

(a)
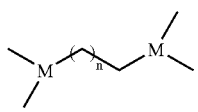
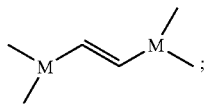
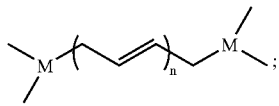

where M is N, P, arsenic or antimony and n is an integer from 1 to about 20;

(b)
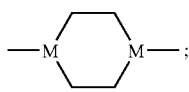 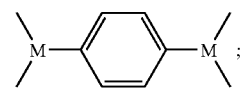
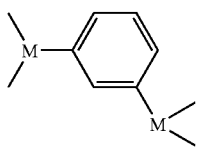
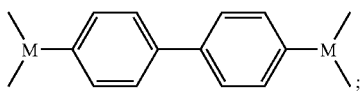
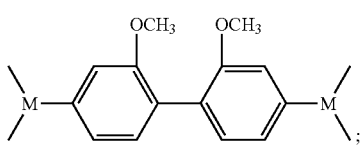
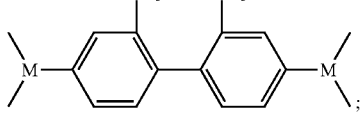

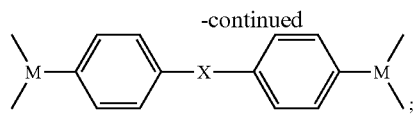

where X is either N, S or P and
where M is as described above.

(c)
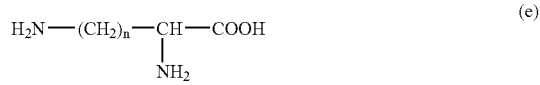

(d)
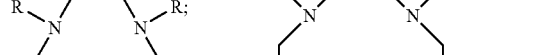

(e)
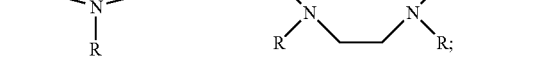

(f)
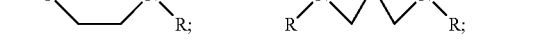

wherein n may be any integer from 1 to about 20 carbon atoms M is either N, P, arsenic or antimony, X is either N, S or P and R is an organic group which is either alkyl, substituted alkyl, alkylacid, aralkyl and alkylaryl.

5. The composition of claim 4 wherein
   the bilinker is selected from the group consisting of N,N,N'N'-tetramethyl-2-butene-1,4-diamine; N,N,N'N'-tetramethylbutane-1,4-diamine; 1,4-dimethyl piperazine; 1,4-phenylenediamine and mixtures thereof.

6. The composition of claim 5 wherein the polyvinyl benzyl halide is polyvinyl benzyl chloride.

7. The composition of claim 6 wherein
   the tri-substituted compound is a halogen atom containing tri-substituted organic compound.

8. The composition of claim 7 wherein the tri-substituted component is selected from the group consisting of tributyl amine, trihexyl amine, triethyl phosphine, tributyl phosphine, trioctyl phosphine and mixtures thereof.

9. The composition of claim 1 wherein the copolymer is the reaction product of polyvinyl benzyl halide and the electron donor.

10. The composition of claim 9 wherein: the π-electron containing copolymer is prepared by the reaction of the polyvinyl benzyl halide with a vinyl polycyclic aromatic hydrocarbon with or without a heteroatom.

11. The composition of claim 9 wherein the polycyclic aromatic hydrocarbon is selected from the group consisting of vinyl naphthalene, vinyl anthracene and mixtures thereof.

12. The composition of claim 1 which corresponds to the formula:
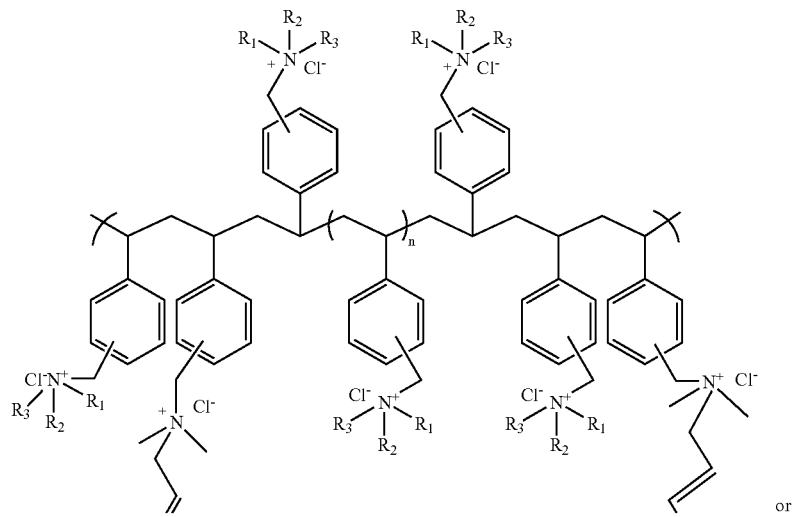
or
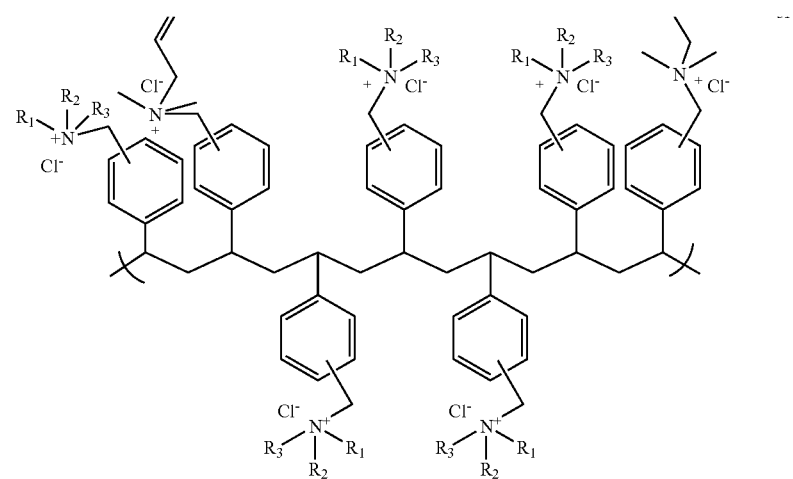
--
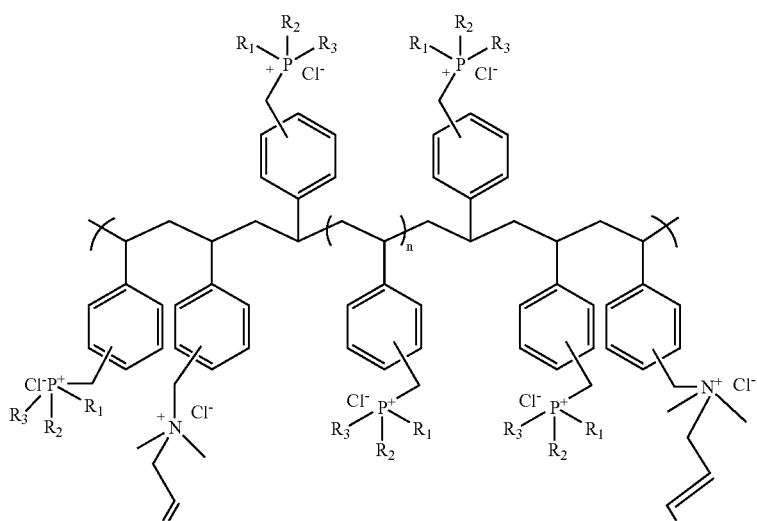

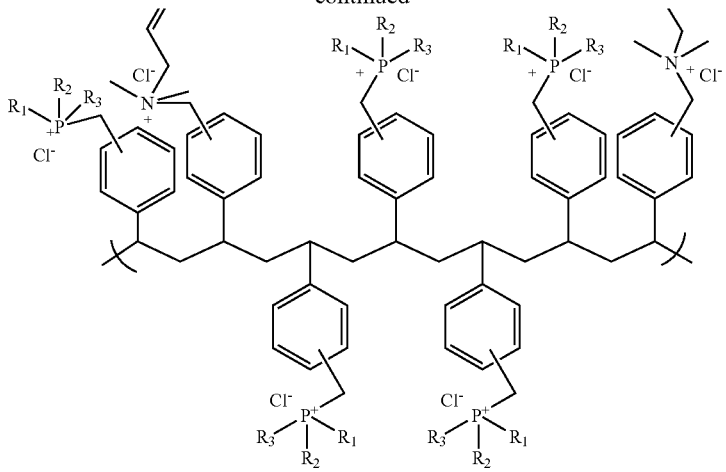

where $R_1$, $R_2$ and $R_3$ are, individually, a straight or branched chain substituted or unsubstituted alkyl group having from 1 to 20 carbon atoms, a straight or branched chain alkyl group having from 1 to 20 carbon atom, substituted or unsubstituted, with one or more of hydroxy, alkoxy, phenoxy; amino or substituted amino, amido, ureido, fluoroalkane, p-fluoroaryl, substituted or unsubstituted monocycloalkyl group having 3 to 12 carbon ring atoms, a substituted monocycloalkyl group having from 3 to about 12 carbon atoms, being substituted with one or more alkyl, alkoxy, or fused benzo groups, a polycycloalkyl group having 2 or more fused rings, each having from 5 to 12 carbon atoms, unsubstituted or substituted with one or more alkyl, alkoxy or aryl groups, an aryl, alkaryl or aralkyl group having at least one ring and from 6 to 20 carbon atoms, unsubstituted or substituted with one or more of alkyl, aryl, fluorine or hydroxy groups, wherein at least two of $R_1$, $R_2$, and R3, together with the quaternary nitrogen atom to which they may be bonded, can form a saturated or unsaturated, unsubstituted or substituted nitrogen-containing, nitrogen and oxygen-containing or nitrogen and sulfur-containing ring having from 3 to 5 carbon atoms, inclusive, and 1 to 3 heteroatoms, inclusive and which may be benzoannulated.

13. A method for enhancing the light output of a chemiluminescent compound which comprises:
admixing with the chemiluminescent composition the enhancer of claim 1.

14. The method of claim 13 wherein the chemiluminescent system compound comprises a 1,2-dioxetane.

15. A method for preparing a compound for enhancing the light output of a chemiluminescent detection compound comprising:
reacting in a substantially one to one molecular ratio a polyvinyl benzyl halide and an organic bilinker in the presence of an organic solvent.

16. The method of claim 15 wherein the bilinker is selected from is selected from the group consisting of:
(a) N,N,N',N'-tetramethyl-2-butene-1,4-diamine,
(b) N,N,N',N'-tetramethylbutane-1,4-diamine,
(c) 1,4-dimethypiperazine,
(d) 1,4-phenylenediamine, and
(e) mixtures thereof.

17. A component for enhancing the light output of a chemiluminescent compound selected from the group consisting of:
(a) the reaction product of polyvinyl benzyl chloride and trioctylphosphine,
(b) the reaction product of polyvinyl benzylchloride and a tributyiphosphine or a trioctyiphosphine;
(c) the reaction product of polyvinyl benzylchloride, fluorescein, a tributyiphosphine and trioctyiphosphine;
(d) the reaction product of a co-polymer of N,N,N',N',tetra methyl-2-butene-1,4-diamine and polyvinyl benzylchloride and (1) trimethylphosphine, (2) tributyiphosphine (3) trioctyiphosphine, (4) a mixture of fluorescein and a tributylphosphine (5) a mixture of a tributylphosphine and a trioctylphosphine, (6) a mixture of fluorescein and a trioctylphosphine, (7) a mixture of fluorescein, a tributylphosphine and trioctylphosphine, (8) tributyl amine, (9) a mixture of tributyl amine and fluorescein,
(e) the reaction product of (polyvinylbenzyl chloride-2-vinylnaphthalene) 95:5 poly and (1) tributyl amine alone or in admixture with fluorescein, (2) a tributylphosphine alone or in admixture with fluorescein, (3) a trioctylphosphine alone or in admixture with fluorescein, (4) mixture thereof, and
(f) mixtures of (a) to (e).

* * * * *